United States Patent [19]

Kambara et al.

[11] Patent Number: 5,163,938

[45] Date of Patent: Nov. 17, 1992

[54] HIGH-FREQUENCY SURGICAL TREATING DEVICE FOR USE WITH ENDOSCOPE

[75] Inventors: Koji Kambara; Toshitaka Hanzawa, both of Hachioji; Tsutomu Okada, Inagi; Tatsuya Saito, Tokyo; Kenichiro Sanagi, Tokyo, all of Japan

[73] Assignee: Olympus Optical Co., Ltd., Tokyo, Japan

[21] Appl. No.: 696,727

[22] Filed: May 7, 1991

[30] Foreign Application Priority Data

Jul. 19, 1990 [JP] Japan .................. 2-191096

[51] Int. Cl.⁵ .............................. A61B 17/39
[52] U.S. Cl. .............................................. 606/47
[58] Field of Search ..................... 606/45–47

[56] References Cited

U.S. PATENT DOCUMENTS

| 4,724,836 | 2/1988 | Okada ............................. 606/46 |
| 4,846,125 | 6/1989 | Frimberger . |
| 5,024,617 | 6/1991 | Karpiel ............................. 606/47 |

FOREIGN PATENT DOCUMENTS

| 87098237 | 7/1982 | Fed. Rep. of Germany . |
| 61-67710 | 5/1986 | Japan . |
| 63-255050 | 10/1988 | Japan . |
| 1235497 | 6/1986 | U.S.S.R. ............................. 606/47 |

Primary Examiner—Lee S. Cohen
Attorney, Agent, or Firm—Frishauf, Holtz, Goodman & Woodward

[57] ABSTRACT

A conductive wire 3 is inserted into a flexible sheath 2 with a wiring portion thereof exposed at a distal end portion of the sheath. Upon the pull of the wire 3, the distal end portion is curved and the exposed wire portion is pull taut to provide a wire portion for incision. A restricting member 5 is provided within the sheath 2 to restrict the direction in which the distal end portion of the sheath 2 is curved. As viewed from the proximal end side to the distal end side of the sheath 2, the wire portion 6 is located within an angle range of 0° to 90° leftwise from the aforementioned direction in a manner to diagonally follow the outer surface of the sheath 2 in a counterclockwise direction to the longitudinal axis of the sheath. An affected region in the body cavity of a human being is incised with a high-frequency current carried through the conductive wire.

13 Claims, 2 Drawing Sheets

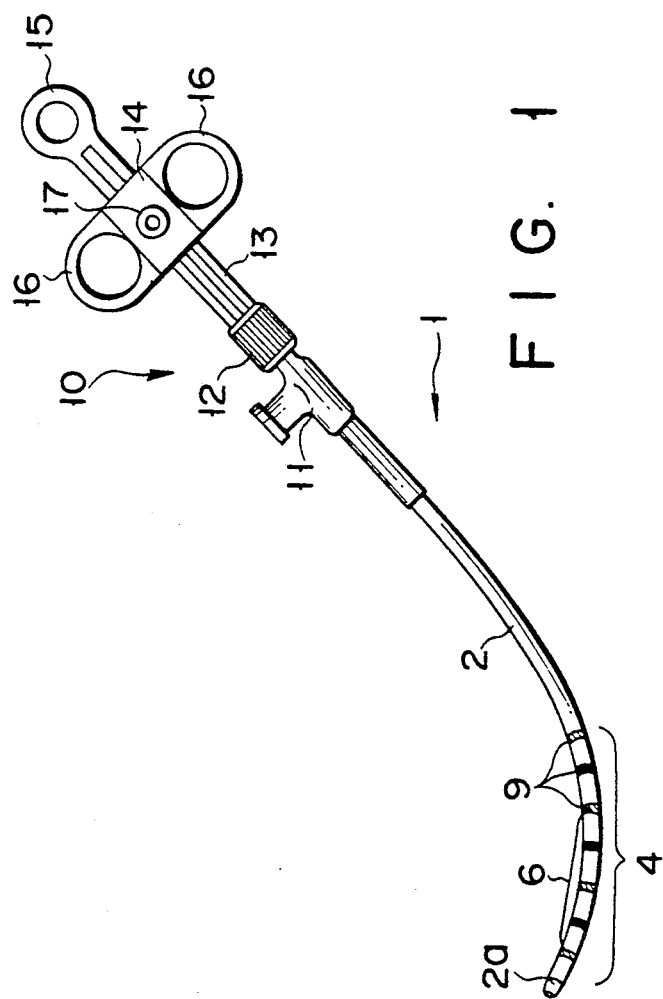
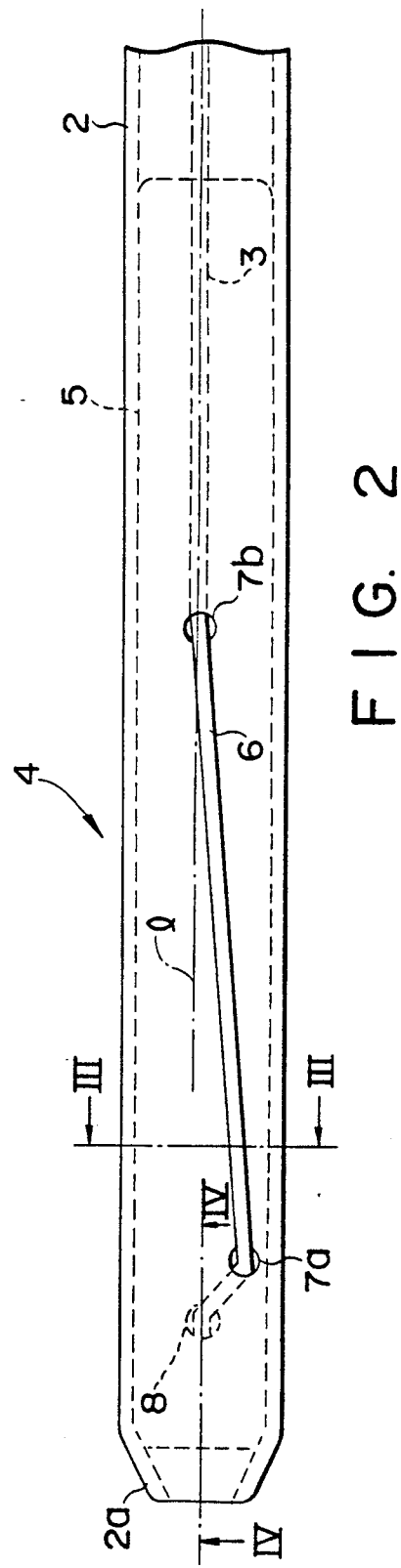

HIGH-FREQUENCY SURGICAL TREATING DEVICE FOR USE WITH ENDOSCOPE

BACKGROUND OF THE INVENTION

1. Field of the Invention

The present invention relates to a high-frequency surgical treating device for use with an endoscope which is inserted through the endoscope into a body cavity of a human subject to incise a tissue region of, for example, the duodenal papillae.

2. Description of the Related Art

A high-frequency surgical knife for incising an affected region of a body cavity of a human subject with the use of a high-frequency current is known, for example, in Published Unexamined Japanese Utility Model 61-67710, DE-GM 8,709,823.7 and Published Unexamined Japanese Patent Application 63-255,050. In these cases, a conductive wire is inserted into a flexible sheath of electrically insulating property such that a wire portion somewhat short of its tip thereof is externally exposed at the distal end portion of the sheath. Upon the pull of the wire, the distal end portion of the sheath is curved.

A high-frequency incising area is provided at a straight cord portion of the exposed wire portion. The incising area is placed in contact with an affected region in a body cavity of a human being and, while being so done, a high-frequency current is flowed in the conductive wire to incise an affected tissue.

When an affected region in the body cavity of a human being is to be incised by this type of high-frequency surgical knife, various problems arise depending upon the situation under which it is involved.

In the case where the output of the biliary duct carrying bile into the duodena, for example, the duodinal papillae, is narrowed by the ulcer, etc., papillo-sphincterotomy (hereinafter referred to as an EST) is generally performed as a operation for incising some sphincter at the end of the biliary duct. If, upon carrying out an incising operation through the EST, some pancreas site is erroneously incised in the situation under which the blood vessels run in the neighborhood of a right side of a region to be incised, there occurs a hemorrhage or pancreatitis is liable to occur due to its hemorrhage.

In order to avoid the situation under which the pancreas site is wrongly incised in an attempt to incise a narrowed area of the duodenal pailae with the use of a high-frequency surgical knife, it is desired that, as viewing the distal end side of the sheath from the proximal (base) side of the sheath, the incising portion of the conductive wire of the high-frequency surgical knife be situated in the second quadrant area (hatched area) in a coordinate plane shown in FIG. 8.

The conventional high-frequency surgical knife, if being incorrectly used, will cause an unfavorable situation as set out below.

The high-frequency surgical knife as disclosed in Published Unexamined Japanese Utility Model 61-67710 is of such a type that the incising portion of the conductive wire incises an affected region 30 in the body cavity of a human subject at a positive side of a Y-axis on the coordinate plane shown in FIG. 8.

The high-frequency surgical knife of DE-GM 8,709,823.7 is of such a type that a stable sheet readily bendable toward a region to be incised is disposed within a sheath so as to provide a stabler bending characteristic to the knife as a whole and an incising operation is stably performed for an affected region 30 while the stable sheet is being positively bent toward the positive side of the Y-axis on the plane shown in FIG. 8.

However, these surgical knives, unless being manufactured with high accuracy, cannot perform an incising operation in a desired direction. Furthermore, the high-frequency incising area of the wire is readily liable to enter the first quadrant area from the Y-axis positive direction side. In order to avoid this situation, a high skill is required on the side of an operator.

In the high-frequency surgical knife of Published Unexamined Japanese Patent Application 63-255050, a coil-like shape memory alloy member is located in the distal end portion of the sheath and, upon being heated, takes on a circumferentially coiled form. If alignment fails to be obtained between the position of an incising area comprised of a conductive wire portion exposed on the outer periphery of the sheath and the position in which the affected region is to be incised, the shape memory alloy member is coiled by heat caused by electric current passed therethrough to turn or twist the distal end portion of the sheath. This, in turn, twists the incising area secured to the sheath to enable the direction of it to be aligned with the direction in which the affected region is to be incised.

In actual practice, it is difficult, however, to accurately control the degree of coiling of the shape memory alloy member. If the extent of coiling is too large, the surgical knife has to be drawn out of the endoscope and again inserted into it, requiring a lot of time. Furthermore, the high-frequency surgical knife becomes complicated in its construction and expensive.

SUMMARY OF THE INVENTION

It is accordingly the object of the present invention to provide a high-frequency surgical treating device for use with an endoscope, which can safely and positively incise an affected region in a body cavity of human being in an assumed coordinate plane and can be so done by a simpler means.

The object of the present invention is achieved by a high-frequency surgical treating device inserted into a body cavity of a human subject through a treating-tool insertion channel of an endoscope to enable an affected region in a body cavity of a human subject to be incised by its incising portion supplied with high-frequency current, which comprises (a) a flexible sheath having a distal end portion, proximal end and longitudinal center axis, the distal end portion being insertable into the body cavity through the insertion channel of the endoscope;

(b) means for controlling the direction in which the distal end portion of the sheath is bent in a direction corresponding to a specified plane;

(c) a conductive wire for operation which is inserted into the sheath;

(d) a wire for high-frequency incision which is electrically connected to the conductive wire and emerges, as an exposed portion, from within the sheath, the high-frequency wire being located on the sheath within an angle range of 0° to 90° leftward from the plane, including the longitudinal center axis, with the longitudinal center axis as a center axis upon viewing the distal end side of the sheath from the proximal side of the sheath and extending away from the plane toward the distal end of the sheath in a manner to be offset counterclockwise from the plane with respect to the longitudinal axis thereof, the pane being a plane in which the distal end portion is curved, whereby the affected region is incised with high-frequency current coming from the conductive wire; and (e) wire operating means for curving the distal end portion of the sheath upon the pull of the conductive wire to provide a high-frequency incision area with the high-frequency incision wire pull taut.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below, serve to explain the principles of the invention FIG. 1 is a perspective view generally showing a high-frequency surgical knife for endoscope, according to an embodiment of the present invention;

FIG. 2 is a plan view showing a distal end portion of the high-frequency surgical knife shown in FIG. 1;

DETAILED DESCRIPTION OF THE PREFERRED EMBODIMENTS

Figure 3:
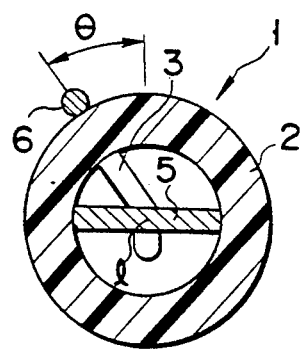
FIG. 3 is a cross-sectional view taken along line III—III in FIG. 2.

One embodiment of the present invention will be explained below with reference to the accompanying drawings.

A high-frequency surgical knife 1 for an endoscope as shown in FIG. 1 includes a flexible sheath 2 of electrically insulating property. An operation section 10 as will be set out below is mounted on the proximal (base) end of the sheath 2. A tip 2a of the sheath 2 is provided as a tapered end. A plurality of distance marks 9 indicating the distance are provided on the outer periphery of a distal end portion 4 of the sheath 2.

A flexible, electrically conductive wire 3 is inserted through a channel of the sheath 2 over a substantially whole length of the sheath. A direction control member 5 made up of a flexible flat sheet is provided in the distal end portion 4 of the sheath 2 such that it extends over a length from the tip 2a back to a location partway of the sheath 2 to restrict the bending or curving direction of the distal end portion 4 of the sheath 2. The direction control member 5 may be so provided in the sheath 2 as to extend over substantially the whole length of the sheath. The distal end portion 5a of the direction control member 5 and tip portion of the sheath 2 are somewhat bent in a direction in which the distal end portion 4 of the sheath 2 is curved upwardly. Since the direction control member 5 has a width somewhat greater than the inner diameter of the sheath 2, it is held under an elastic force of the sheath 2 with its opposite side edges firmly contacting with the inner wall surface of the sheath 2. The way of holding the direction control member 5 relative to the sheath is not restricted only to one as set out above and various holding methods may be considered instead. For example, the direction control member 5 may have its opposite side edges buried in the wall of the sheath or bonded there.

Figure 7:
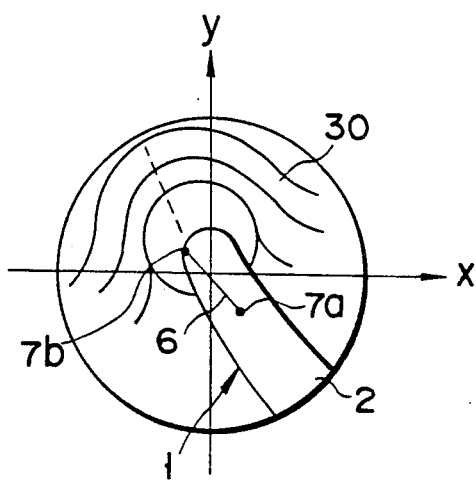
FIG. 7 is an explanative view diagrammatically showing the manner in which an affected region in a body cavity of a human being is incised with the high-frequency surgical knife of the present invention.
Figure 8:
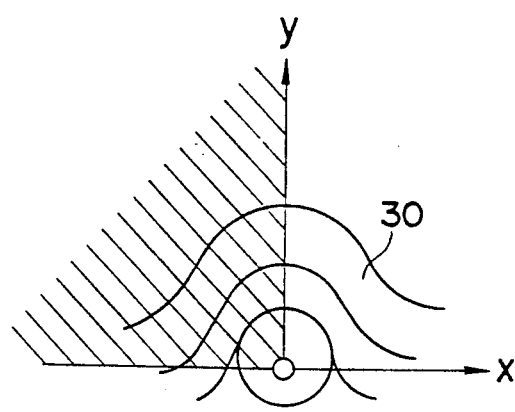
FIG. 8 is an explanative view diagrammatically showing an affected region of a human being in a coordinate plane and a conventional high-frequency surgical knife.

As shown in FIG. 2, a pair of through holes 7a, 7b are offset in the distal end portion 4 of the sheath 2 in a direction of a longitudinal axis l of the sheath 2, but with a hole-to-hole line not in a direction parallel to the longitudinal axial direction as shown in FIG. 2. That is, the through hole 7a provided on the distal end (or tip) side of the sheath 2 is counterclockwise shifted relative to the through hole 7b provided on the proximal (or base) end side of the sheath 2 as viewed from the proximal end to the distal end of the sheath. As shown in FIG. 7, the through hole 7a is located within a second quadrant area with a coordinate plane plotted on the sheath 2 a viewed from the proximal end side to the distal end side of the sheath. The through hole 7a on the distal end side of the sheath is counterclockwise displaced or offset at an angle of, for example, 30° to 60° relative to the through hole 7b on the proximal side. As shown in FIGS. 2 and 3, with the longitudinal axis of the sheath 2 as a center, the through hole 7a on the distal end side is located at an angle $\theta$ of 30° to 60° counterclockwise from a plane perpendicular to the lateral direction (horizontal direction) of the direction control member 5, the plane including the longitudinal center axis. Further, the through hole 7b on the rear end side is located at an angle $\theta$ of 90° from a plane corresponding to the lateral direction (horizontal direction) of the direction control member 5, that is, is set in a plane perpendicular to the lateral direction (horizontal direction) of the direction control member 5 in which case the plane includes the longitudinal center axis l of the sheath 2.

Figure 4:
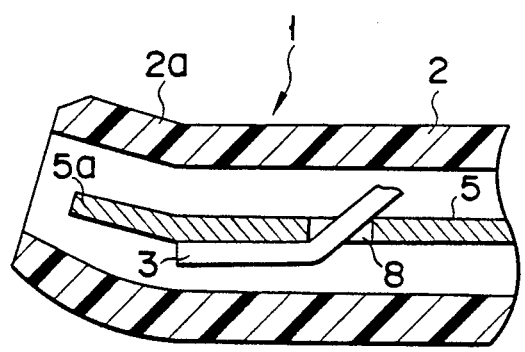
FIG. 4 is a cross-sectional view taken along line IV—IV in FIG. 2.

An intermediate portion of the wire 3 is exposed out of the sheath 2 at an area between the pair of through holes 7a and 7b. As shown in FIG. 4, the distal end portion of the wire 3 is mounted on the direction control member 5 that it is located near the distal end 5a of the direction control member 5. Then the distal end portion of the wire 3 extends out of the sheath 2 via the through hole 7a situated on the distal end side of the sheath and into the sheath 2 via the through hole 7b on the base end side of the sheath with an exposed loop left between the through holes 7a and 7b. The outwardly exposed wire portion left as the exposed loop constitutes a wire portion 6 for incision by a high-frequency wave. The wire portion 6 of the wire 3 extends such that it is curved, at an area between the through holes 7a and 7b, with respect to the longitudinal direction of the sheath 2. That is, as shown in FIG. 2, the wire portion 6 is not parallel to the longitudinal direction of the sheath 2 and is curved along a direction from the through hole 7b on the base end side toward the through hole 7a on the distal end side of the sheath 2. The exposed wire portion 6, viewed from the base end side toward the distal end side of the sheath 2, is displaced counterclockwise around the longitudinal center axis 1 as tracing is made from the through hole 7b toward the through hole 7a. Stated in another way, the through hole 7a is located within the second quadrant area on the coordinate plane as viewed from the base end side toward the distal end side of the sheath 2 as shown in FIG. 7.

As shown in FIG. 4, the tip of the wire 3 passes through the through hole 8 provided in the direction control member 5 and is fixed to the rear surface of the direction control member 5.

Figure 5:
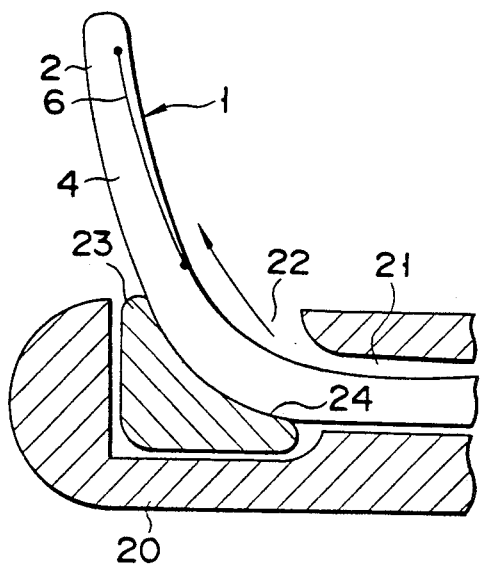
FIG. 5 is a longitudinal cross-sectional view showing the distal end portion of an endoscope through which the high-frequency surgical knife of the present invention is inserted.
Figure 6:
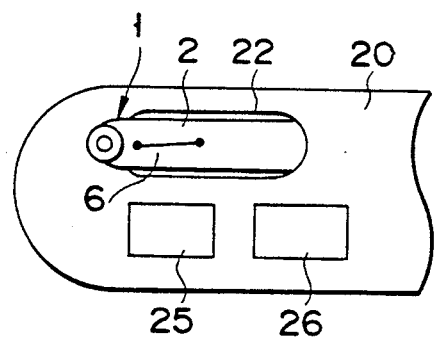
FIG. 6 is a plan view showing a distal end portion of the endoscope having a treating-tool insertion channel through which the high-frequency surgical knife of the present invention is inserted.

The base end portion of the wire 3 extends through the channel of the sheath 2 back to the operation section 10. The operation member 10 includes a connector member 11 attached to the base end of the sheath 2. The guide bar 13 is coupled by an annular mount ring 12 to the connector member 11. The operation member 14 is slidably mounted on the guide bar 13. A finger engaging ring 15 is provided at the rear end of the guide bar 13 and a pair of finger engaging rings 16, 16 are provided at the operation member 14. The rear end of the wire 3 is connected to the operation member 14. The operation member 14 includes an electric terminal 17 through which electric current is conducted to the wire 3. A feed cord, not shown, leading to a high-frequency power source (not shown) is connected to the electric terminal 17. If the operation member 14 is slidably moved along the guide bar 13, then the wire 3 can be pushed ahead or withdrawn back. In FIGS. 5 and 6, reference numeral 20 denotes an endoscope having a raising base member 23 within an open end portion 22 of a treating-tool channel 21. The raising base member 23 has a guide surface 24 for guiding the sheath 2 to allow the sheath to extend forward. Reference numeral 25 shows an observation window and 26 an illumination window.

Performing an EST using a high-frequency surgical knife 1 for an endoscope will be explained below.

The sheath 2 of the high-frequency surgical knife 1 is inserted through the endoscope into the body cavity of the human subject. If any affected region to be treated is found under an observation on the endoscope 2, the distal end portion 4 of the sheath 2 is projected from the distal end side opening 22 of the endoscope's channel 21 into the body cavity along the guide surface 24 of the raising base member 23 provided in the opening 22 of the channel 21. The distal end portion 4 of the sheath 2 is curved upon being projected along the guide surface 24 of the raising base member 23. That is, the direction control member 5 inserted into the sheath 2 and held in the distal end portion 4 of the sheath 2 is curved, in a direction perpendicular to a plane (width direction) in which the direction control member 5 is curved most easily, and restricts the curving of the distal end portion 4 of the sheath in the direction perpendicular to that plane. With the curving direction of the distal end portion 4 so restricted, the distal end portion 4 of the sheath 2 is slidably guided along the guide surface 24 of the raising base member 23 to allow it to be raised in a vertical direction to the guide surface 24 after it has been moved along the guide surface 24. In this way, the distal end portion 4 of the sheath 2 is so raised in a manner to have it positively oriented at the guide surface 24 of the raising base member. For this reason, the distal end portion 4 of the sheath 2 is stably projected out of the endoscope 20 via the opening 22. Since, at this time, the direction control member 5 is curved in the direction perpendicular to the width direction set out above, the wire portion 6 for incision is located, as viewing the distal end portion 4 of the sheath 2 as shown in FIG. 7, in an angle range of 0° to 90° counterclockwise from the direction in which the distal end portion 4 of the sheath 2 is curved. That is, the wiring section 6 for incision is located in the second quadrant region in the coordinate plane as shown in FIG. 7. In this state, the wire portion 6 of the high-frequency surgical knife approaches the affected region 30 and, when the wire 3 is drawn by operating the operation member 14 connected to the base (proximal) end of the wire 3, the distal end portion 4 of the sheath 2 is curved toward the affected region 30 and into contact with the affected region. At this state, the wire portion 6 is located within the second quadrant region in the coordinate plane as shown in FIG. 7, not in the first quadrant region which should be avoided. The wiring portion 6 thus located and oriented is supplied with a high-frequency current, while being placed in contact with the affected region 30 of the human subject, to incise the region 30. At that time, the high-frequency current is supplied from a high-frequency current source.

When the high-frequency surgical knife 1 for endoscope is used in the EST, it is possible, according to the present invention, to prevent a tissue region from being incised at a first quadrant region, a region which is dangerous at that time. It is, therefore, possible to achieve the positive incision of an affected region 30 alone, under the previously defined restricted action by the direction control member 5, a region which is safe in the EST, and to do so safely under a proper restricted action by the direction control member. Furthermore, since the direction control member 5 of the present invention is made of a simple sheet-like member, a high-frequency surgical knife 1 of simpler construction is obtained at low cost according to the present invention.

Since the wire portion 6 for incision can be curved or turned counterclockwise toward the tip of the sheath 2 as viewed in the longitudinal axis of the sheath 2 (see FIG. 2), it is moved far away from the first quadrant region in the coordinate plane, as shown in FIG. 7, and has its tip portion located more surely within the second quadrant region, enabling an affected region of a human subject to be incised more positively by the wiring portion 6.

A separate wire member may be used as a wire 3 to be inserted through the sheath 2 so long as it is electrically connected to the wire portion 6 for incision.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A high-frequency surgical treating device insertable into a body cavity of a human subject through a treating-tool insertion channel of an endoscope to enable an affected region in a body cavity of a human subject to be incised by an incising portion of the surgical treating device which is supplied with a high-frequency current, the surgical treating device comprising:

(a) a flexible sheath having a distal end portion at a distal end side of the sheath, a proximal end at a proximal side of the sheath, and a longitudinal center axis, the distal end portion of the sheath being insertable into the body cavity through the insertion channel of the endoscope;

(b) means for controlling the direction in which the distal end portion of the sheath is bent in a direction corresponding to a specified plane;

(c) an electrically conductive wire for operation which is inserted into the sheath;

(d) a wire for high-frequency incision which is electrically connected to the electrically conductive wire and which emerges, as an exposed portion, from within the sheath, the high-frequency incision wire being located on the sheath within an angle range of greater than 0° and equal to or less than 90° counterclockwise from the plane, including the longitudinal center axis, with the longitudinal center axis as a center axis upon viewing the distal end side of the sheath from the proximal side of the sheath and extending away from the plane toward the distal end portion of the sheath in a manner to be offset counterclockwise from the plane with respect to the longitudinal axis thereof, the plane being a plane in which the distal end portion is curved, whereby the affected region is incised with a high-frequency current flowing through the conductive wire; and (e) wire operating means for curving the distal end portion of the sheath upon pulling of the conductive wire toward the proximal end of the sheath, to thereby provide a high-frequency incision area with the high-frequency incision wire pulled taut.

2. The high-frequency surgical treating device according to claim 1, wherein the distal end portion of said sheath has a forward and rearward through holes, the forward through hole and backward through hole, the high-frequency incision wire emerging from within the distal end portion of said sheath via the backward through hole and entering the distal end portion of said sheath via the forward through hole.

3. The high-frequency surgical treating device according to claim 2, wherein, as viewed from the proximal side toward the distal end side of the sheath, the forward through hole is located within an angle range of from 30° to 60° leftward from the plane including the longitudinal center axis, with the longitudinal center axis as a center, and the backward through hole is located in a smaller angle range than the forward through hole.

4. The high-frequency surgical treating device according to claim 3, wherein, as viewed from the proximal side to the distal end side of the sheath, said backward through hole is located in said plane.

5. The high-frequency surgical treating device according to claim 1, wherein said means for controlling the direction includes a member provided in the sheath and having a property so as to be able to be curved in a specific direction so as to curve the distal end portion of the sheath.

6. The high-frequency surgical treating device according to claim 1, wherein said means for controlling the direction includes a sheet-like member provided within the sheath, the sheet-like member having a flexible property in a direction perpendicular to its plane and being so arranged as to have said direction located in a direction in which the distal end portion of the sheath is to be curved.

7. A high-frequency surgical treating device insertable into a body cavity of a human subject through a treating-tool insertion channel of an endoscope to enable an affected region in a body cavity of a human subject to be incised by an incising portion of the surgical treating device which is supplied with a high-frequency current, the surgical treating device comprising:

(a) a flexible sheath having a distal end portion at a distal end side of the sheath, a proximal end at a proximal side of the sheath, and a longitudinal center axis, and being insertable into the body cavity through the treating-tool insertion channel;

(b) a flat sheet, arranged in a section of the sheath which includes the distal end portion of the sheath, for restricting a bending direction of the sheath;

(c) a pair of through holes formed in said section of the sheath so as to face the flat sheet, one of said through holes being at a rear side of said section and located on a plane which includes the longitudinal center axis of the sheath and is substantially perpendicular to the flat sheet when viewing a distal end of the sheath from a proximal end thereof, and the other of said through holes being at a front side of said section and located within an angle range greater than 0° and equal to or less than 90° counterclockwise from said plane;

(d) an electrically conductive wire, which is arranged in the sheath, said conductive wire having a leading end portion exposed outside of the sheath through said pair of through holes, for incising the affected region in the body cavity upon supply of high-frequency current to said conductive wire; and (e) wire operating means for curving the distal end portion of the sheath by pulling a rear end portion of said conductive wire such that the exposed portion of said conductive wire is tightly drawn to provide a high-frequency incision area.

8. The high-frequency surgical treating device according to claim 7, wherein a leading end of the leading end portion of said conductive wire is affixed to the flat sheet.

9. The high-frequency surgical treating device according to claim 8, wherein, the leading end of said conductive wire is affixed to the flat sheet, on the longitudinal center axis of the sheath.

10. The high-frequency surgical treating device according to claim 9, wherein the flat sheet has a through hole formed therein, the through hole of the flat sheet being located on the longitudinal center axis of the sheath, and wherein the leading end of the conductive wire is inserted into the through hole of the flat sheet and is affixed to a rear surface of the flat sheet.

11. The high-frequency surgical treating device according to claim 7, wherein the flat sheet has a width greater than an inner diameter of the sheath.

12. The high-frequency surgical treating device according to claim 7, wherein the through hole at the front side of said section in which the flat sheet is arranged is located within an angle range of from 30° to 60° counterclockwise from said plane.

13. The high-frequency surgical treating device according to claim 7, wherein the distal end portion of the sheath is tapered.

* * * * *